United States Patent [19]

Petitpierre

[11] 4,100,169

[45] Jul. 11, 1978

[54] THIAZOLYLPHTHALIDE COMPOUNDS

[75] Inventor: Jean Claude Petitpierre, Kaiseraugst, Switzerland

[73] Assignee: Ciba-Geigy Corporation, Ardsley, N.Y.

[21] Appl. No.: 629,156

[22] Filed: Nov. 5, 1975

[30] Foreign Application Priority Data

Nov. 14, 1974 [CH] Switzerland ........................ 15189/74

[51] Int. Cl.[2] ............................................ C07D 277/38

[52] U.S. Cl. ......................... 260/306.8 R; 260/302 H; 282/27.5; 427/152; 427/153; 428/307; 428/323; 428/327; 428/913; 428/914

[58] Field of Search ............... 428/323, 327, 306, 307, 428/308, 913, 914; 427/152, 153; 260/306.8 R, 302 H; 282/27.5

[56] References Cited

U.S. PATENT DOCUMENTS

| | | | |
|---|---|---|---|
| 3,287,381 | 11/1966 | De Cat | 260/306.8 R |
| 3,901,918 | 8/1975 | Koga | 260/306.8 R |

FOREIGN PATENT DOCUMENTS

| | | | |
|---|---|---|---|
| 314,206 | 5/1956 | Fed. Rep. of Germany | 260/306.8 R |

*Primary Examiner*—Ellis Robinson
*Attorney, Agent, or Firm*—Edward McC. Roberts; Prabodh I. Almaula

[57] ABSTRACT

Thiazolylphthalide compounds of the general formula

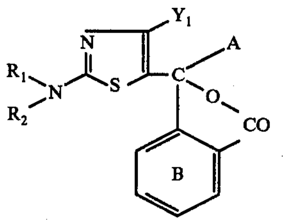

(1)

wherein A represents a p-aminophenyl radical of formula

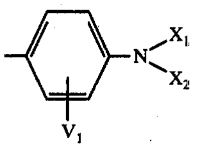

(1a)

or a 3-indolyl radical of formula

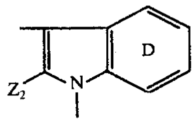

(1b)

or a 2-thiazolyl radical of formula

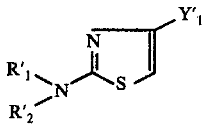

(1c)

each of $R_1$, $R_2$, $X_1$, $X_2$, $R_1'$ and $R_2'$ independently represents hydrogen, alkyl of 1 to 12 carbon atoms, alkoxyalkyl of 2 to 8 carbon atoms, cycloalkyl of 5 or 6 carbon atoms, or unsubstituted or substituted benzyl or phenyl, or each pair of substituents $R_1$ and $R_2$, $X_1$ and $X_2$ or $R_1'$ and $R_2'$, together with the nitrogen atom to which they are attached, independently represents a heterocyclic ring, each of $Y_1$ and $Y_1'$ represents hydrogen, alkyl of 1 to 12 carbon atoms, cycloalkyl or 5 or 6 carbon atoms or unsubstituted or substituted benzyl or phenyl, $V_1$ represents hydrogen, alkyl of 1 to 12 carbon atoms, alkoxy of 1 to 12 carbon atoms or acyloxy of 2 to 12 carbon atoms, $Z_1$ represents hydrogen, alkyl of 1 to 12 carbon atoms, benzyl or $\beta$-cyanoethyl, $Z_2$ represents hydrogen, alkyl of 1 to 12 carbon atoms or phenyl, and wherein the benzene rings B and D can be further substituted by halogen, nitro or by an amino group which is unsubstituted or substituted by alkyl of 1 to 6 carbon atoms.

These thiazolylphthalide compounds are particularly usful as color formers which give strong red, violet, blue or green colorations when they are brought into contact with an electron-accepting co-reactant.

8 Claims, No Drawings

THIAZOLYLPHTHALIDE COMPOUNDS

The present invention provides new thiazolylphthalide compounds, a process for their manufacture and a method of using them in pressure-sensitive or thermoreactive recording systems.

The thiazolylphthalide compounds of the present invention have the formula (1)

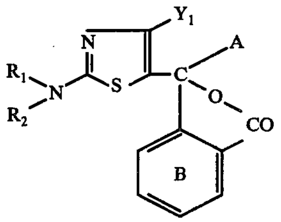

wherein A represents a p-aminophenyl radical of formula (1a)

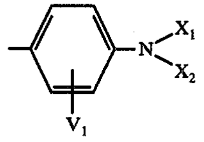

or a 3-indolyl radical of formula (1b)

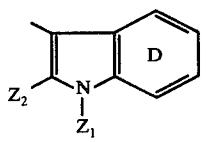

or a 2-thiazolyl radical of formula (1c)

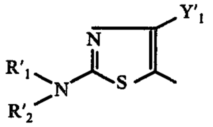

each of $R_1$, $R_2$, $X_1$, $X_2$, $R_1'$ and $R_2'$ independently represents hydrogen, alkyl of 1 to 12 carbon atoms, alkoxyalkyl of 2 to 8 carbon atoms, cycloalkyl of 5 or 6 carbon atoms, or unsubstituted or substituted benzyl or phenyl, or each pair of substituents $R_1$ and $R_2$, $X_1$ and $X_2$ or $R_1'$ and $R_2'$, together with the nitrogen atom to which they are attached, independently represents a heterocyclic ring which optionally contains a further heteroatom, each of $Y_1$ and $Y_1'$ represents hydrogen, alkyl of 1 to 12 carbon atoms, cycloalkyl of 5 or 6 carbon atoms or unsubstituted or substituted benzyl or phenyl, $V_1$ represents hydrogen, alkyl of 1 to 12 carbon atoms, alkoxy of 1 to 12 carbon atoms or acyloxy of 2 to 12 carbon atoms, $Z_1$ represents hydrogen, alkyl of 1 to 12 carbon atoms, benzyl or β-cyanoethyl, $Z_2$ represents hydrogen, alkyl of 1 to 12 carbon atoms or phenyl, and wherein the benzene rings B and D can be further substituted by halogen, nitro or by an amino group which is unsubstituted or is substituted by alkyl of 1 to 6 carbon atoms.

Alkyl groups represented by $R_1$, $R_2$, $Y_1$, $X_1$, $X_2$, $V_1$, $Z_1$, $Z_2$ and $Y_1'$, $R_1'$ and $R_2'$ can be straight-chain or branched. Examples of such alkyl groups are:

methyl, ethyl, n-propyl, isopropyl, n-butyl, sec.butyl, n-hexyl, n-octyl or n-decyl. Alkoxyalkyl groups represented by R or X substituents can contain 1 to 4 carbon atoms in each of the alkyl moieties. Preferred alkoxyalkyl radicals are β-methoxyethyl or β-ethoxyethyl. Cycloalkyl represented by R, Y and X substituents is cyclopentyl or preferably cyclohexyl. Examples of substituents which may be present in the benzyl or phenyl group are alkyl of 1 to 4 carbon atoms, alkoxy of 1 to 4 carbon atoms, alkoxycarbonyl of 2 to 5 carbon atoms, acyl of 1 to 4 carbon atoms, nitro, halogens, or amino groups which are substituted by alkyl of 1 to 4 carbon atoms or benzyl or are unsubstituted. Halogen is preferably fluorine or bromine and is most preferably chlorine. Examples of these araliphatic and aromatic radicals are: p-methylbenzyl, o- or p-chlorobenzyl, o- or p-nitrobenzyl, o- or p-tolyl, xylyl, o- or p-chlorophenyl, o- or p-nitrophenyl.

A heterocyclic radical represented by each of the pair of substituents $R_1$ and $R_2$, $X_1$ and $X_2$ and $R_1'$ and $R_2'$, together with the nitrogen atom to which they are attached, can contain 3 to 15, preferably 5 or 6, ring members. The heterocyclic radical is, for example, a pyrrolidinyl, piperidino, pipecolino, perhydroazepinyl, heptamethylenimino, octamethylenimino, 1,2,3,4-tetrahydroquinolinyl, indolinyl or hexahydrocarbazolyl group. The heterocyclic radical can also contain two heteroatoms, in which case it is, for example, a morpholino, thiomorpholino, piperazino group, a N-alkylpiperazino group containing 1 to 4 carbon atoms in the alkyl moiety, or a pyrazolinyl or 3-methylpyrazolinyl group.

As alkoxy, $V_1$ represents preferably methoxy or ethoxy. Acyloxy represented by $V_1$ is most preferably alkanoyloxy of 2 to 4 carbon atoms, for example acetyloxy or propionyloxy.

The benzene rings B and D can contain dimethylamino, diethylamino or n-hexylamino as substituted amino groups. As halogen, B and D can contain fluorine, bromine or especially chlorine. Preferably B and D are not further substituted, but B can advantageously also contain chlorine.

Preeminent compounds of the general formula (1) have the following general formula (2)

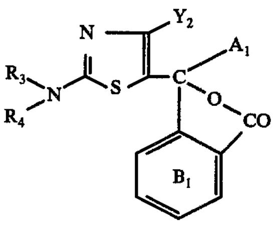

wherein $A_1$ represents a p-aminophenyl radical of formula (2a)

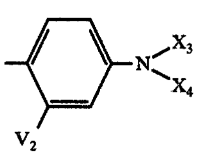

or a 3-indolyl radical of formula (2b)

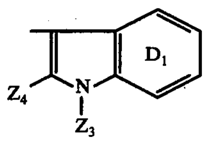

or a 2-thiazolyl radical of formula (2c)

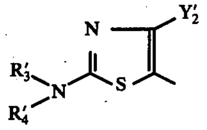

each of $R_3$, $R_4$, $X_3$, $R_3'$ and $R_4'$ independently represents hydrogen, alkyl of 1 to 12 carbon atoms, phenyl or benzyl, or each of the pair of substituents $R_3$ and $R_4$, $X_3$ and $X_4$ or $R_3'$ and $R_4'$, together with the nitrogen atom to which they are attached, independently represents a 5- or 6-membered heterocyclic ring which can contain a further heteroatom, for example an oxygen, sulphur or nitrogen atom, as ring member, each of $Y_2$ and $Y_2'$ represents hydrogen, alkyl of 1 to 4 carbon atoms or phenyl which may be substituted by halogen, nitro, alkyl, alkoxy or dialkylamino, each containing 1 to 4 carbon atoms in the alkyl moiety, $V_2$ represents hydrogen, alkyl of 1 to 4 carbon atoms, alkoxy of 1 to 4 carbon atoms or alkanoyloxy of 2 to 4 carbon atoms, $Z_3$ represents hydrogen, alkyl of 1 to 12 carbon atoms or benzyl $R_4$ represents hydrogen, alkyl of 1 to 4 carbon atoms or phenyl, and wherein the benzene rings $B_1$ and $D_1$ can be further substituted by halogen, nitro or by dialkylamino containing 1 to 4 carbon atoms in each alkyl moiety.

Particularly useful thiazolylphthalide compounds of the above formulae (1) and (2) are those listed hereinafter under A), B) and C):

A) 3-p-aminophenyl-3-thiazolylphthalide compounds of the general formula (3)

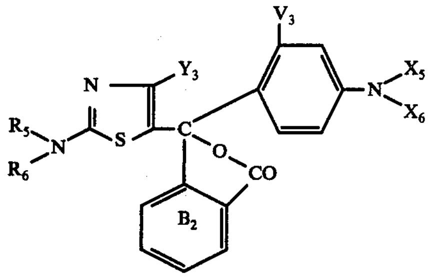

wherein each of $R_5$, $R_6$ and $X_5$ independently represents alkyl of 1 to 8 carbon atoms, phenyl or benzyl, $X_6$ represents hydrogen, alkyl of 1 to 4 carbon atoms or benzyl, or each of the pair of substituents $R_5$ and $R_6$ and $X_5$ and $X_6$, together with the nitrogen atom to which they are attached, independently represents a piperidino, morpholino or preferably a pyrrolidinyl radical, $Y_3$ represents methyl or phenyl, $V_3$ represents hydrogen, methyl, alkoxy of 1 to 4 carbon atoms or alkanoyloxy of 2 to 4 carbon atoms, and wherein the benzene ring $B_2$ is unsubstituted or contains 1 to 4 chlorine atoms;

B) 3-thiazolyl-3-indolyl-phthalide compounds of the general formula (4)

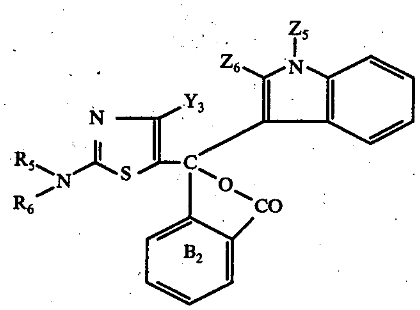

wherein $B_2$, $R_3$, $R_6$ and $Y_3$ are as defined in formula (3), $Z_5$ represents alkyl of 1 to 12 carbon atoms or benzyl, and $Z_6$ represents methyl or phenyl;

C. 3,3-bis-thiazolyl-phthalide compounds of the general formula (5)

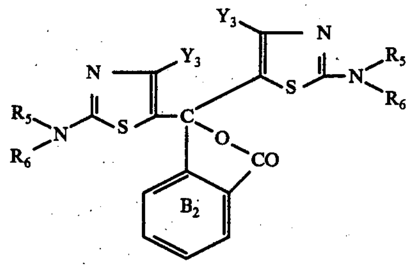

wherein $R_2$, $R_5$, $R_6$ and $Y_3$ are as defined in formula (3).

The thiazolylphthalide compounds of formulae (1) to (5) are obtained by processes which are known per se. One process for the manufacture of the thiazolylphthalide compounds of formula (1) comprises reacting, in optional sequence, 1 mole of a phthalic anhydride of formula (6)

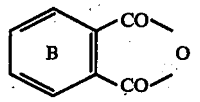

with 1 mole of a compound of formula A-H (7) and 1 mole of a thiazole compound of formula (8)

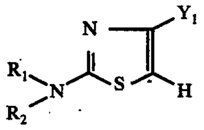

wherein A, B, $R_1$, $R_2$ and $Y_1$ are as defined hereinbefore.

Thiazolylphthalide compounds of the general formula (1), wherein A represents a radical of formula (1a) or (1b), are advantageously manufactured by first reacting the phthalic anhydride of formula (6) with a p-aminobenzene compound of the general formula

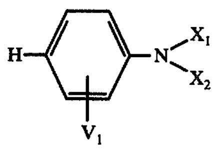
(7a)

or with an indole compound of formula

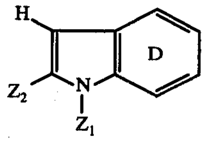
(7b)

in an equimolar ratio, and then reacting further the reaction product of the general formula

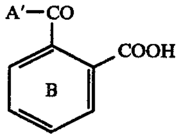
(9)

with a thiazole compound of the general formula (8), wherein B, D, $Z_1$, $Z_2$, $X_1$, $X_2$ and $V_1$ are as defined hereinbefore and A' has the formula (1a) or (1b). The first step is preferably carried out in the presence of an organic solvent, for example toluene, benzene or xylene or a chlorobenzene, at temperatures between 50° and 150° C. The reaction of the reaction product of formula (9) with the thiazole compound of formula (8) is advantageously carried out at a temperature of 10° to 100° C, preferably in the presence of an acid condensing agent. Examples of suitable condensing agents are acetic anhydride, sulphuric acid, zinc chloride or phosphoroxy chloride.

The thiazolylphthalide compounds of formula (1), wherein A represents a thiazolyl radical of formula (1c), can be manufactured in two steps if it is desired to obtain asymmetrical products. Symmetrical compounds are advantageously obtained in a single step by reacting the phthalic anhydride of formula (6) with the thiazole compound of formula (8) in a molar ratio of 1:2.

The thiazolylphthalide compounds of formulae (1) to (5) are colourless compounds which are suitable for use as colour formers when brought into contact with an acid active substance, i.e., an electron acceptor substance. Typical examples of such coreactants are attapulgite clay, silton clay, silica, bentonite, halloysite, aluminium oxide, aluminium sulphate, aluminium phosphate, kaolin or any acid clay, or an acid polymeric material, for example a phenolic polymer, an alkylphenolacetylene resin, a maleic acid/rosin resin or a partially or completely hydrolysed polymer of maleic acid and styrene, ethylene, vinyl methyl ether or carboxypolymethylene. Preferred coreactants are attapulgite clay, silton clay or phenolformaldehyde resin. These electron acceptors are preferably applied in the form of a layer to the face of the receiver sheet.

It is possible to produce different colours with these colour formers, mostly strong red, violet, blue or green colourations. When used with other known colour formers, they are also useful for obtaining grey or black tints.

The thiazolylphthalides of the present invention constitute a novel class of colour formers whose solubilities are such that a wide choice of solvents is available for encapsulating and other purposes. This can be advantageous for example when encapsulating the colour formers.

The colour formers of this invention are suitable above all for use in pressure-sensitive copying and recording material. Such a material comprises for example at least a pair of sheets that contain at least one colour former of formulae (1) to (5) dissolved in an organic solvent, and an electron acceptor as developer. The colour former effects a coloured marking at those points at which it comes into contact with the electron acceptor substance.

These colour formers which are present in the pressure-sensitive copying material are separated from the electron acceptor substance in order to prevent them from becoming active too soon. This can be accomplished as a rule by incorporating the colour formers in foam-like, sponge-like or honeycomb-like structures. Preferably, however, the colour formers are enclosed in microcapsules which can be burst by pressure.

When the capsules are burst by pressure, for example with a pencil, and the colour former solution is thus transferred to an adjacent sheet which is coated with an electron acceptor, a coloured zone is produced. This new colour results from the dye which is thereby formed and which absorbs in the visible range of the electromagnetic spectrum.

A number of processes for the manufacture of microcapsules have long been known. Such known processes are described, for example, in U.S. Pat. Nos. 2,183,053, 2,797,201, 2,800,457, 2,800,458, 2,964,331, 3,016,308, 3,171,878, 3,265,630, 3,405,071, 3,410,250, 3,418,656, 3,424,827 and 3,427,250. Further processes are described in British patent 989,264 and above all in British Patent Nos. 1,156,725, 1,301,052 and 1,355,124. All these and other processes are suitable for encapsulating the colour formers of the present invention.

The colour formers are encapsulated preferably in the form of solutions in organic solvents. Examples of suitable solvents are preferably non-volatile solvents, for example polyhalogenated diphenyl, such as trichlorophenyl and a mixture thereof with liquid paraffin, tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of naphthalene or diphenyl, terphenyls, partially hydrogenated terphenyl, or other chlorinated or hydrogenated condensed aromatic hydrocarbons. The capsule walls can be formed evenly around the droplets of the colour former solution by coacervation, in which case the encapsulating material can consist of gelatin and gum arabic, as described e.g. in U.S. Pat. No. 2,800,457.

The capsules can be formed preferably also from an aminoplast or from modified aminoplasts by polycondensation, as described in the British patents cited above.

A preferred arrangement consists in applying the encapsulated colour formers as a layer to the back of a transfer sheet and the electron acceptor substance as a layer to the face of a receiving sheet. It is also possible to add other known colour formers, for example crystal violet lactone, 3,3-bis-(1'-n-octyl-2'-methylindol-3'-yl)-phthalide or benzoylleucomethylene blue.

The microcapsules containing the colour formers of formula (1) can be used for the manufacture of pressure-sensitive copying materials of the most widely different known kinds. The various systems differ substantially from one another in the arrangement of the capsules and the colour reactants and in the carrier material.

The microcapsules can be contained in a bottom layer of the top sheet and the developer in the coating layer of the bottom sheet. The components can, however, also be used in the paper pulp. Another arrangement of the constituents consists in the microcapsules containing the colour former and the developer being in or on the same sheet in the form of one or more single layers or in the paper pulp.

Such pressure-sensitive copying materials are described, for example, in U.S. Pat. Nos. 2,730,457, 2,932,582, 3,418,250, 3,418,656, 3,427,180 and 3,516,846. Further systems are described in British Patent Nos. 1,042,596, 1,042,597, 1,042,598, 1,042,599, 1,053,935 and 1,517,650. Microcapsules which contain the colour formers of formula (1) are suitable for each of these systems and for other systems.

The capsules are preferably secured to the carrier by means of a suitable adhesive. Since paper is the preferred carrier material, these adhesives are principally paper coating agents, for example gum arabic, polyvinyl alcohol, hydroxymethyl cellulose, casein, methyl cellulose or dextrin.

The term "paper" used herein comprises not only normal paper made from cellulose fibres, but also paper in which the cellulose fibres are replaced (partially or completely) by synthetic polymer fibres.

The thiazolylphthalides of the present invention can also be used in a thermoreactive recording material. This contains normally at least a carrier, a colour former, an electron acceptor substance and optionally a binder. Thermoreactive recording systems comprise heat-sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks.

The thermoreactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor substance at those points at which heat is applied and the desired colour develops.

The developers are the same electron-accepting substances as are used in pressure-sensitive papers. For practical purposes the developer should be solid at room temperature and melt or soften above 50° C. Examples of such products are the clays or phenolic resins already mentioned, or phenolic compounds, for example 4-tert.butylphenol, 4-phenylphenol, 4-hydroxydiphenyl oxide, α-naphthol, β-naphthol, 4-hydroxybenzoic acid methyl ester, 4-hydroxyacetophenol, 2,2'-dihydroxydiphenyl, 4,4-isopropylidene-diphenol, 4,4'-isopropylidene-bis-(2-methylphenol), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, e.g. tartaric acid, oxalic acid, maleic acid, citric acid, citraconic acid or succinic acid.

Fusible, film-forming binders are preferably used for the manufacture of the thermoreactive recording material. These binders are usually soluble, whereas the thiazolylphthalides and the developer are insoluble in water. These binders should be able to disperse and fix the colour former and the developer at room temperature.

By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylic amide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyl resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further additives. The coatings can contain, for example, talc, $TiO_2$, ZnO or $CaCO_3$ for improving the degree of whiteness, facilitating the printing of papers, and for preventing the heated pen from sticking. In order to effect the colour formation only within a limited temperature range, it is possible to add substances such as urea, thiourea, acetanilide, phthalic anhydride or other appropriate fusible products which induce the simultaneous melting of the colour former and developer.

Typical thermoreactive recording materials in which the colour formers according to the invention can be used are described, for example, in German Offenlegungsschriften 2,110,864 and 2,228,581, in French Patent No. 1,524,826 and in Swiss Patent Nos. 164,976, 407,185, 444,196 and 444,197.

The following Examples illustrate the invention, the percentages being by weight unless otherwise stated.

EXAMPLE 1

A mixture of 20.4 g of 2-dimethylamino-4-phenylthiazole, 7.4 g of phthalic anhydride and 150 ml of acetic anhydride is stirred for 20 hours at 100° C. The cooled solution is diluted with 700 ml of water and extracted three times withchloroform. The chloroform solutions are dried over magnesium sulphate and concentrated. The resultant product is then recrystallised from a mixture of cyclohexane and toluene. Yield: 26.8 g of a compound of formula (10)

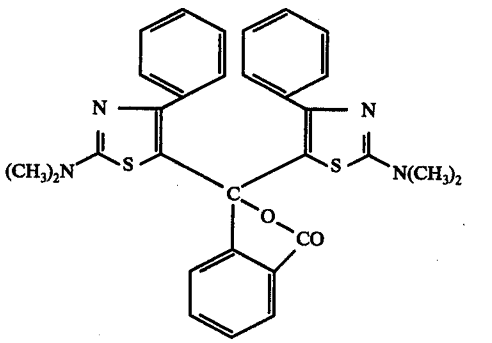

Melting point: 121°-122° C. Absorption maximum (λ max.) in 95% acetic acid = 642 nm. When the compounds is applied to a paper coated with silicon clay a turquoise colour with an absorption maximum λ at 648 nm is obtained.

EXAMPLE 2

The procedure of Example 1 is repeated using 14.2 g of 2-dimethylamino-4-methylthiazole instead of 2-dimethylamino-4-phenylthiazole. Yield: 7.9 g of the compound of formula (11)

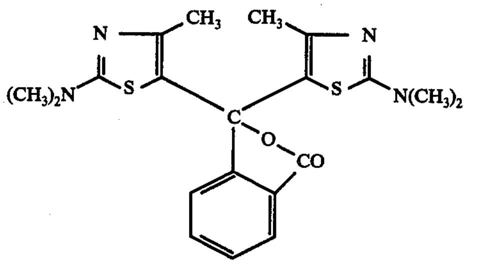

Melting point: 220°-222° C. λ max. in 95% acetic acid = 572 nm. This colour former develops on silton clay a reddish blue shade with an absorption maximum of 576 nm.

EXAMPLE 3

The procedure of Example 1 is repeated using 14.3 g of tetrachlorophthalic anhydride instead of phthalic anhydride. Yield: 13.2 g of the compound of formula (12)

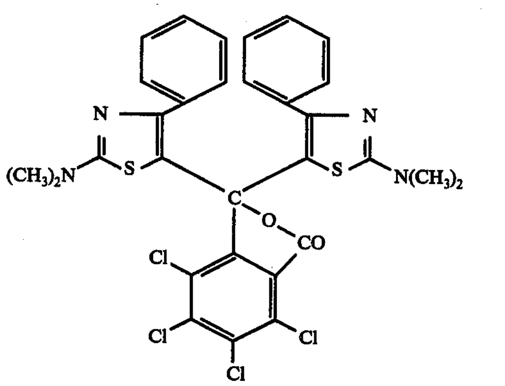

Melting point: 228°-230° C. λ max. in 95% acetic acid = 637 nm. On silton clay this colour former develops a blue shade with an absorption maximum λ of 643 nm.

EXAMPLE 4

6.15 g of 1-ethyl-3-(2'-carboxybenzoyl)-2-methylindole and 2.84 g of 2-dimethylamino-4-methylthiazole are added to 20 ml of acetic anhydride and heated for 30 minutes to 50° C. The solution is diluted with 150 ml of water and extracted three times with chloroform. The chloroform solutions are dried and concentrated and the resultant product is recrystallised from toluene. Yield: 7.6 g of the compound of formula (13)

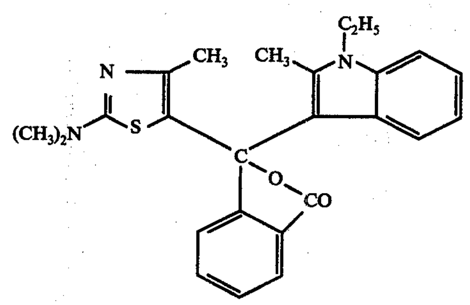

Melting point: 206°-208° C. λ maximum in 95% acetic acid = 562 nm. A violet colour with an absorption maximum λ of 565 nm is obtained on silton clay.

EXAMPLE 5

The procedure of Example 4 is repeated using 4.08 g of 2-dimethylamino-4-phenylthiazole instead of 2-dimethylamino-4-methylthiazole. Yield: 8 g of the compound of formula (14)

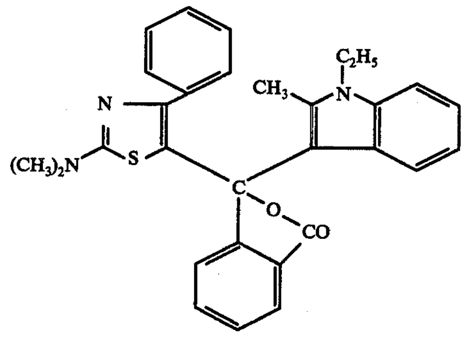

Melting point: 138°-139°. λ maximum in 95% acetic acid = 598 nm. On silton clay this colour former produces a greenish blue colour with an absorption maximum of 611 nm.

EXAMPLE 6

A mixture of 6.75 g of 2-(2'-carboxybenzoyl)-5-pyrrolidino-phenetol, 2.84 g of 2-dimethylamino-4-methylthiazole and 40 ml of acetic anhydride is stirred for 1 hour at 40° C. The reaction mixture is poured into 600 ml of water and the resultant precipitate is filtered off. Recrystallisation of the reaction product from cyclohexane yields 6.9 g of the compound of formula

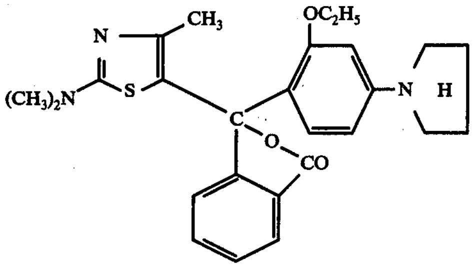

(15)

Melting point: 124°-126° C. λ maximum in 95% acetic acid = 600 nm. On contact with silton clay this colour former produces a green shade with an absorption maximum of 614 nm.

EXAMPLE 7

The procedure of Example 6 is repeated using 6.8 g of 2-(2'-carboxybenzoyl)-5-diethylaminophenol instead of 2-(2'-carboxybenzoyl)-5-pyrrolidinophenetol. Yield: 8.3 g of the compound of formula

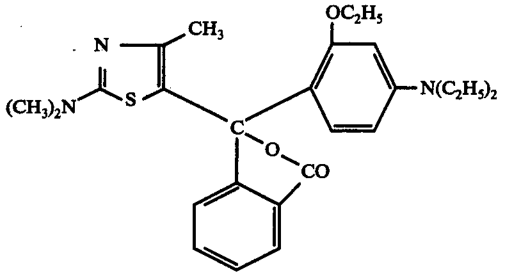

(16)

Melting point: 106°-109° C. λ maximum in 95% acetic acid = 597 nm. On silton clay this colour former develops a green shade with an absorption maximum of 610 nm.

EXAMPLE 8

The procedure of Example 7 is repeated using 4.08 g of 2-dimethylamino-4-phenylthiazole instead of 2-dimethylamino-4-methylthiazole. Yield: 8.8 g of the compound of formula

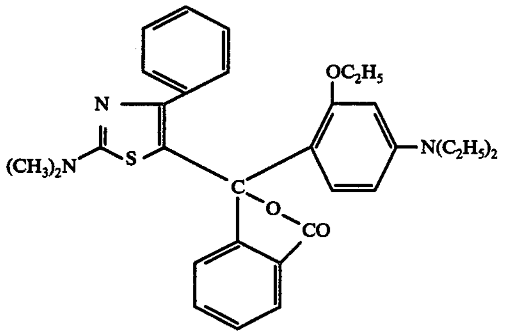

(17)

Melting point: 185°-186° C. λ maximum in 95% acetic acid = 645 nm. On silton clay this colour former develops a green shade with an absorption maximum of 650 nm.

EXAMPLE 9

The procedure of Example 1 is repeated using 9.7 g of 4-nitrophthalic anhydride instead of phthalic anhydride to yield an isomeric mixture of formula (18) in which the nitro groups are in 5- and 6-positions.

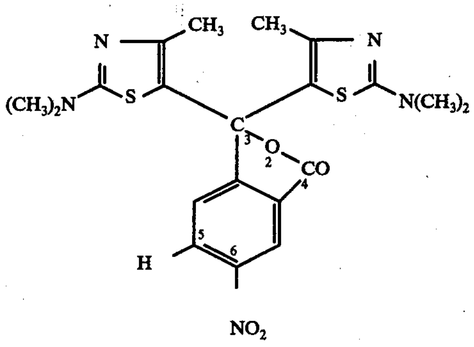

(18)

Melting point: 84°-86° C. λ maximum in 95% acetic acid = 578 nm.

EXAMPLE 10

The procedure of Example 4 is repeated using 7.4 g of 1-benzyl-3-(2'-carboxybenzoyl)-2-methylindole instead of 1-ethyl-3-(2'-carboxybenzoyl)-2-methylindole. Yield: 5.1 g of the compound of formula

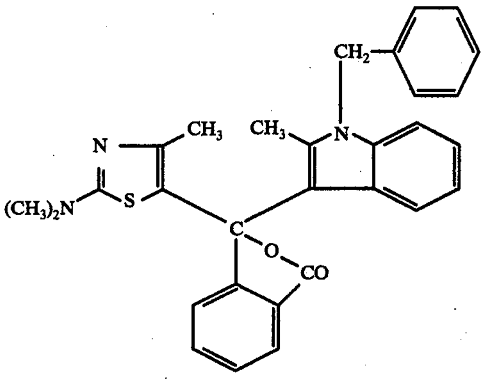

(19)

Melting point: 211°-212° C. λ maximum in 95% acetic acid = 556 nm. A violet shade with an absorption maximum of 560 nm is obtained on silton clay.

EXAMPLE 11

The procedure of Example 4 is repeated using 7.84 g of 1-n-octyl-3-(2'-carboxybenzoyl)-2-methylindole instead of 1-ethyl-3-(2'-carboxybenzoyl)-2-methylindole. Yield: 2.2 g of the compound of formula

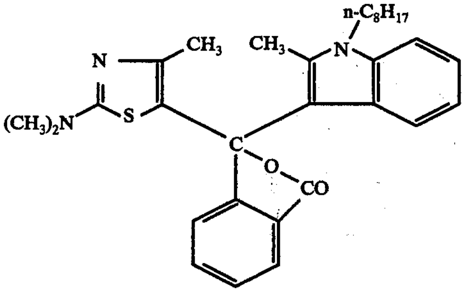

(20)

Melting point: 59° C. λ maximum in 95% acetic acid = 561 nm. A violet shade with an absorption maximum of 565 nm is obtained on silton clay.

EXAMPLE 12

Manufacture of a pressure-sensitive copying paper

A solution of 3 g of the thiazolylphthalide compound of formula (15) in 97 g of partially hydrogenated terphenyl is emulsified in a solution of 12 g of pigskin gelatin in 88 g of water of 50° C. A solution of 12 g of gum arabic in 88 g of 50° C is then added and then 200 ml of water of 50° C. The resultant emulsion is poured into 600 g of ice water and cooled until the temperature is 20° C, in the course of which the coacervation is effected. A sheet of paper is coated with the resultant suspension of microcapsules and dried. A second sheet of paper is coated with silton clay. The first sheet and the sheet of paper coated with silton clay are laid on top of each other with the coated sides face to face.

Writing by hand or with a typewriter on the first sheet produces a green copy on the coreactive sheet.

Corresponding effects can be obtained by using each of the other colour formers of Examples 1 to 5 or 7 to 11.

EXAMPLE 13

Manufacture of a thermoreactive paper 6 g of an aqueous dispersion which contains 1.57% of the thiazolylphthalide of formula (14) and 6.7% of polyvinyl alcohol are mixed with 134 g of an aqueous dispersion which contains 14% of 4,4-isopropylidene-diphenol and 6% of polyvinyl alcohol. This mixture is applied to a paper and dried. Contacting the paper with a heated ball-point pen produces a vivid greenish blue colour.

Similar results are obtained on using any of the other colour formers obtained in Examples 1 to 4 and 6 to 11.

I claim:

1. A thiazolylphthalide compound of the formula

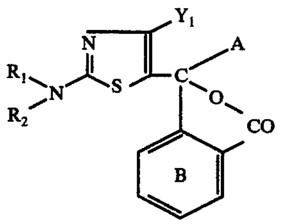

(1)

wherein A represents a p-aminophenyl radical of formula

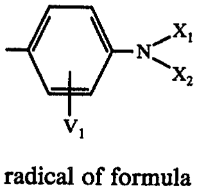

(1a)

or a 3-indolyl radical of formula

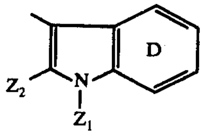

(1b)

or a 2-thiazolyl radical of formula

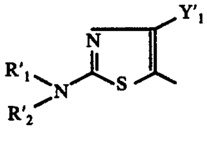

(1c)

each of $R_1R_2$, $X_1$, $X_2$, $R_1'$ and $R_2'$ independently represents hydrogen, alkyl of 1 to 12 carbon atoms, alkoxyalkyl of 2 to 8 carbon atoms, cycloalkyl of 5 or 6 carbon atoms, or unsubstituted or substituted benzyl or phenyl wherein the substituents are independently selected from the group consisting of alkyl of 1 to 4 carbon atoms, alkoxy of 1 to 4 carbon atoms, alkoxycarbonyl of 2 to 5 carbon atoms, acyl of 1 to 4 carbon atoms, nitro, halogen and amino substituted by alkyl of 1 to 4 carbon atoms or benzyl, each of $Y_1$ and $Y_1'$ represents hydrogen, alkyl of 1 to 12 carbon atoms, cycloalkyl or 5 or 6 carbon atoms or said unsubstituted or substituted benzyl or phenyl, $V_1$ represents hydrogen, alkyl of 1 to 2 carbon atoms, alkoxy of 1 to 12 carbon atoms or acyloxy of 2 to 12 carbon atoms, $Z_1$ represents hydrogen, alkyl of 1 to 12 carbon atoms, benzyl or $\beta$-cyanoethyl, $Z_2$ represents hydrogen, alkyl of 1 to 12 carbon atoms or phenyl, and wherein the benzene rings B and D independently are unsubstituted or substituted by halogen, nitro or by an amino group which is unsubstituted or substituted by alkyl of 1 to 6 carbon atoms.

2. The thiazolylphthalide compound of claim 1 wherein each of $R_1$, $R_2$, $X_1$, $R_1'$, and $R_2'$ independently represents hydrogen, alkyl of 1 to 12 carbon atoms, phenyl or benzyl, each of $Y_1$ and $Y_1'$ represents hydrogen, alkyl of 1 to 4 carbon atoms, phenyl, or phenyl substituted by halogen, nitro, alkyl, alkoxy or dialkylamino, each containing 1 to 4 carbon atoms in the alkyl moiety, $V_1$ represents hydrogen, alkyl of 1 to 4 carbon atoms, alkoxy of 1 to 4 carbon atoms or alkanoyloxy of 2 to 4 carbon atoms, $Z_1$ represents hydrogen, alkyl of 1 to 12 carbon atoms or benzyl, $Z_2$ represents hydrogen, alkyl of 1 to 4 carbon atoms or phenyl, and wherein the benzene rings B and D independently are unsubstituted or substituted by halogen, nitro or dialkylamino containing 1 to 4 carbon atoms in each alkyl moiety.

3. The thiazolylphthalide compound of claim 1 of the formula

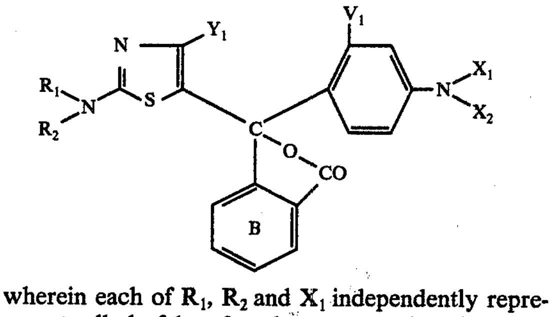

wherein each of $R_1$, $R_2$ and $X_1$ independently represents alkyl of 1 to 8 carbon atoms, phenyl or benzyl, $X_2$ represents hydrogen, alkyl of 1 to 4 carbon atoms or benzyl, $Y_1$ represents methyl or phenyl, $V_1$ represents hydrogen, methyl, alkoxy of 1 to 4 carbon atoms or alkanoyloxy of 2 to 4 carbon atoms, and wherein the benzene ring B is unsubstituted or contains 1 to 4 chlorine atoms or a nitro group.

4. The thiazolyphthalide compound of claim 3 wherein each of $R_1$, $R_2$ and $X_1$ independently is alkyl of 1 to 4 carbon atoms or benzyl, $V_1$ is hydrogen or ethoxy and $X_2$ is hydrogen, alkyl of 1 to 4 carbon atoms or benzyl and wherein the benzene ring B is unsubstituted.

5. The thiazolylphthalide compound of claim 1 of the formula

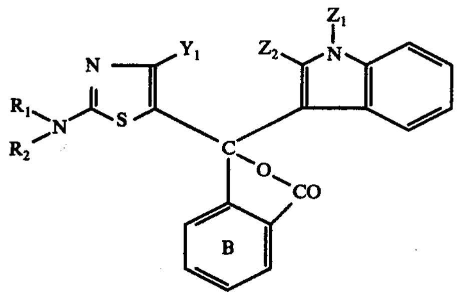

wherein the benzene ring B is unsubstituted or substituted by 1 to 4 clorine atoms or a nitro group, $R_1$ and $R_2$ independently represent alkyl of 1 to 8 carbon atoms, phenyl or benzyl, $Y_1$ represents methyl or phenyl, $Z_1$ represents alkyl of 1 to 12 carbon atoms or benzyl, and $Z_2$ represents methyl or phenyl.

6. The thiazolylphthalide compound of claim 5 wherein $R_1$ and $R_2$ independently are alkyl of 1 to 4 carbon atoms or benzyl, $Z_1$ represents alkyl of 1 to 8 carbon atoms or benzyl and $Z_2$ represents methyl and wherein the benzene ring B is unsubstituted.

7. The thiazolylphthalide compound of claim 1 of the formula

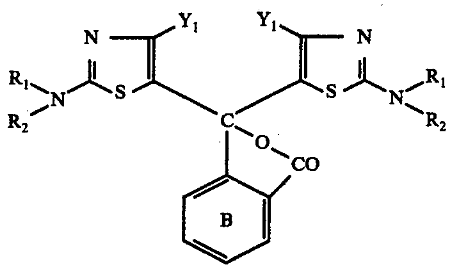

wherein the benzene ring B is unsubstituted or substituted by 1 to 4 chlorine atoms or a nitro group, $R_1$ and $R_2$ independently represent alkyl of 1 to 8 carbon atoms, phenyl or benzyl, and $Y_1$, represents methyl or phenyl.

8. The thiazolylphthalide of claim 7, wherein each of $R_1$ and $R_2$ independently is alkyl of 1 to 4 carbon atoms or benzyl.

* * * * *